(12) United States Patent
Kuppuswamy et al.

(10) Patent No.: US 7,632,953 B2
(45) Date of Patent: Dec. 15, 2009

(54) PROCESS FOR THE PREPARATION OF GABALACTAM

(75) Inventors: Nagarajan Kuppuswamy, Bangalore (IN); Sivaramakrishnan Hariharan, Bangalore (IN); Arulselvan Mariadas, Bangalore (IN)

(73) Assignee: Hikal Limited, Bangalore (IN)

( * ) Notice: Subject to any disclaimer, the term of this patent is extended or adjusted under 35 U.S.C. 154(b) by 268 days.

(21) Appl. No.: 10/535,278

(22) PCT Filed: Nov. 20, 2002

(86) PCT No.: PCT/IN02/00225

§ 371 (c)(1),
(2), (4) Date: Feb. 15, 2006

(87) PCT Pub. No.: WO2004/046108

PCT Pub. Date: Jun. 3, 2004

(65) Prior Publication Data

US 2006/0135789 A1     Jun. 22, 2006

(51) Int. Cl.
*C07D 209/54* (2006.01)
*A61K 31/4015* (2006.01)

(52) U.S. Cl. .................... 548/408; 514/409
(58) Field of Classification Search ........... 548/408; 514/409
See application file for complete search history.

(56) References Cited

U.S. PATENT DOCUMENTS 4,024,175 A     5/1977    Satzinger et al.
5,068,413 A  *  11/1991   Steiner et al. ............. 562/507
5,091,567 A     2/1992    Herrmann et al.

\* cited by examiner

*Primary Examiner*—Kamal A Saeed
*Assistant Examiner*—Shawquia Young

(57) ABSTRACT

The present invention provides an improved process for the preparation of gabalactam of formula 1

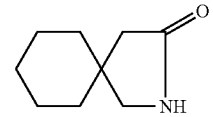

1 that includes preparing an aqueous solution of an alkali or alkaline earth metal hydroxide, adding bromine to the resulting solution to give an appropriate alkali or alkaline earth metal hypobromite; adding an amide of the formula 4

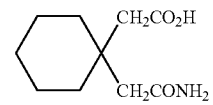

4 aging the resultant mixture; heating the mixture to a temperature in a range of 80 to 100 degrees C.; extracting with nonpolar solvent and distilling under reduced pressure to obtain gabalactam.

16 Claims, No Drawings

PROCESS FOR THE PREPARATION OF GABALACTAM

This invention relates an improved process for the preparation of gabalactam. Gablacatam is chemically known as 2-azaspiro((4,5)decan-3-one. Gabalactam has the structural formula 1 given below.

1

Gabalactam is useful as a starting material for the well-known anti-epileptic and analgesic, 1-aminomethylcyclohexane-1-acetic acid, commonly known as gabapentin which has the structural formula 2.

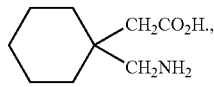

2

It is also a starting material for some of the compounds of structural formula 3

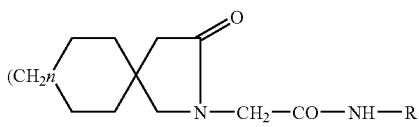

3 wherein R is a hydrogen atom or a saturated or unsaturated lower aliphatic radical and n is 0, 1 or 2 reported in U.S. Pat. No. 4,228,179, with antiepileptic activity. Gabalactam of the formula 1 was first synthesized by Sircar in the laboratory in 1928 (J. Ind. Chem. Soc., 1928, 5, 549; Chem. Abstracts, 1929, 23, 818). Specifically, Sircar carried out a Hofmann Reaction on the mono amide of cyclohexane-1,1-diacetic acid of the formula 4

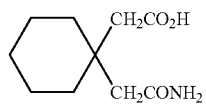

4 with alkaline sodium hypobromite at 55 degrees centigrade for 2 hours. The reaction solution was acidified with HCl and evaporated to dryness. The residue was washed with ether to remove free organic acids and then extracted with acetone. The acetone extract was evaporated to dryness. The residue was neutralized with alkali and extracted into ether. Evaporation of this extract is claimed to give gabalactam in 46% yield.

The process published by Sircar (1928) though not hazardous, results only in 46% yield of gabalactam. The process is not useful for the commercial manufacture of gabalactam because of the number of steps involved and the low yield of gabalactam, making the process expensive and unviable for commercial production of gabapentin for which gabalactam is the penultimate and crucial intermediate.

But some commercial processes for its preparation have appeared later (U.S. Pat. Nos. 4,152,326 & 5,091,567 equivalent to PCT Int. Application no 9914184A & U.S. Pat. No. 5,068,413) which are explained below.

U.S. Pat. No. 4,152,326 discloses that treatment of N-benzene sulfonyloxy-1,1-cyclohexane di acetic acid imide with an alcoholic solution of sodium ethylate gives gabalactam.

U.S. Pat. No. 5,091,567 (and PCT Int. Application 9914184A) discloses that gabalactam can be made from cyclohexanone in 3 steps:

1. Addition of the Wittig Reagent from triethylphosphono acetate to cyclohexanone to give ethyl cyclohexylidene acetate.
2. Additon of nitromethane to the ethyl cyclohexylidene obtained to form ethyl 1-nitromethylcyclohexane acetate and
3. Catalytic reduction of the nitro methyl derivative.

U.S. Pat. No. 5,068,413 discloses that gabalactam can be obtained from cyclohexanone in 4 steps as follows:

1. Conversion of cyclohexanone into diethyl cyclohexylidene malonate.
2. Addition of cyanide to form diethyl 1-cyanocyclohexyl malonate.
3. Hydrolysis of diethyl 1-cyanocyclohexyl malonate to 1-cyanocyclohexyl malonic acid and
4, Catalytic hydrogenation of the 1-cyanocyclohexyl malonic acid at elevated temperature resulting in decarboxylative lactamisation.

Thus, in the processes described in U.S. Pat. No. 5,091,567 and PCT Int. Application no 9914184A, hazardous nitromethane and costly wittig re-agents are used. An explosive and inflammable hydrogen gas and pyrrophoric catalyst such as 10% Pd—C are used in the third step.

In U.S. Pat. No. 5,068,413; the disadvantages are handling of highly poisonous sodium cyanide in the second step and use of expensive rhodium or pyrophoric Raney Nickel as catalyst in the final step.

U.S. Pat. No. 4,152,326 suffers from the fact that one needs to handle corrosive benzene sulfonyl chloride and sodium ethoxide, both of which are toxic inflammable re-agents.

Very recently a process for the preparation of gabapentin has been disclosed in the Indian Patent 186285, In the Example 1 given in the said patent for the preparation of crude 1(amino methyl) cyclohexane acetic acid hydrochloride (commonly known as gabapentin hydrochloride), a reference has been made to the preparation of 2-aza spiro(4,5) decane-3 one (commonly known as gabalactam) by using standard Hoffman reaction conditions starting from the amide of the formula 4. When we followed the said procedure for the preparation of 2-aza spiro(4,5) decane-3 one (commonly known as gabalactam), the process gave very unsatisfactory results as explained below.

We carried out the Hoffmann reaction on the amide of the formula 4 using bromine and varying strengths of sodium hydroxide solution. At the end of the reaction, the solution was acidified with HCl. The acidic solution was extracted with methylene chloride and the methylene chloride layer evaporated to dryness. The residue which has been stated to be gabalactam in the Example 1 of the said patent, was actually a thick gum showing the presence of gabalactam by analytical methods such as HPLC. This product did not solidify even upon seeding with standard gabalactam, which is a very nice crystalline solid, melting at 88-92 deg C. The gum was also found to be highly acidic and upon neutralization with alkali, gabalactam was liberated in the solid form. It thus appeared that the product extracted from the acidified Hoffmann Reaction solution might be the hydrochloride of gabalactam and not gabalactam itself as has been stated in the Example 1 of the said patent. The gummy product was subjected to HPLC. Although gabalactam was found to be the major component, other impurities were present, one of them more polar with a RRT (Relative Retention Time) to a significant extent. Area % purity was determined in three experiments and in one (namely Example no 1) gabalactam content (wt %) was also determined. The results are given below:

| No. | Amide of The formula 4 In grams | Wt (g) & strength (% w/w) of NaOH Solution | | Bromine in ml | Yield of Gummy product | Purity as Gabalactam area % |
|---|---|---|---|---|---|---|
| 1. | 100 | 215 | 40 | 26 | 49 | 85* |
| 2. | 200 | 430 | 50 | 52 | 73 | 72 |
| 3. | 100 | 215 | 73 | 26 | 70 | 85 |

*Gabalactam content 42 g.

The results of the above experiments very clearly indicate that under the conditions described in the Indian Patent 186285 the yield and the purity of 2-aza spiro(4,5) decane-3 one (commonly known as gabalactam) obtained is no better than the initial experiments described by Sarcar in 1928. Further the Example is silent on the yield and purity of 2-aza spiro(4,5) decane -3 one. Therefore the said Indian Patent does not fulfill the need for a process for synthesizing the important & crucial intermediate Gabalactam in higher yields (more than 70%) and of high purity (more than 95%), which are essential conditions for its production commercially so that the process can be used directly for the preparation of Gabapentin.

Upon more detailed investigations, we observed, surprisingly that the highly alkaline solution (pH 11-13) from the Hoffmann Reaction already contained free gabalactam of the formula 1 which could be conveniently extracted into nonpolar hydrocarbon solvents like toluene, ethylene dichloride, methylene dichloride and hexane. Aqueous washing of the organic layer followed by evaporation gave a major crop (more than 55%) of gabalactam. The alkaline layer was heated again and worked up with organic solvents to give more of the lactam to offer a total yield of more than 70% by theory. Since the lactam was extracted from a highly alkaline solution, acidic impurities, which are significant contaminants in the previously disclosed acidic workup according to the process disclosed in the above Example 1 mentioned Indian patent, are avoided, conferring an additional advantage of higher purity (more than 95% by HPLC).

Accordingly, the present invention provides an improved process for the preparation of gabalactam of the formula 1

which comprises
(i) preparing an aqueous solution of an alkali or alkaline earth hydroxide in a concentration ranging from 10 to 20% by weight, adding bromine to the resulting solution to give the appropriate alkali or alkaline earth hypobromite solution having a concentration ranging from 5 to 10% by weight,
(ii) adding 1 part by weight of an amide of the formula 4

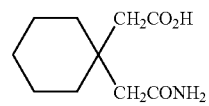

to 7.5 to 9.5 parts by weight, of the solution of the alkali or alkaline earth metal hypobromite obtained in step (i) during a period in the range of 1-4 hours, at a temperature in the range of −10 to +10 degrees C.,
(iii) keeping the resultant mixture for aging in the temperature in the range of −10 to +10 degree C. for a period in the range of 0.5 to 2 hours,
(iv) heating the mixture gradually to a temperature in the range of 80 to 100 degrees C., for a period in the range of 3 to 8 hours and aging for 5 to 8 hours,
(v) cooling the reaction mixture to a temperature in the range of 30 to 50 degrees C.,
(vi) extracting the mixture using a nonpolar solvent or a mixture thereof,
(vii) subjecting the resulting aqueous layer to the steps of (iv) to (vi) defined above,
(viii) combining the organic layers obtained in steps (vi) & (vii) together,
(ix) washing resulting combined organic layers with water at a temperature in the range of 30-35 degree C., and
(x) distilling of the organic solvent at a temperature in the range of 60-110 degrees C., under reduced pressure.

In a preferred embodiment of the present invention the various steps in the process can be carried out as follows In the step (i), preferably an alkali metal hydroxide, more preferably sodium hydroxide may be used, The concentration of the solution may preferably range from 10 to 15% more preferably 12.5%. The concentration of the hypobromite may preferably be in the range of 5 to 8% and more preferably 7% by weight.

In the step (ii) the amount of hypobromite added may preferably be 8 to 9 parts, more preferably 8.5 to 9 parts of the solution of sodium hypobromite. The addition may be effected preferably during a period ranging form 1-3 hours, more preferably 1-2 hours. The temperature during the addition may be maintained at preferably −5 to +5 degrees C., more preferably −5 to 0 degrees C., and in step (iii) aging the reaction mixture in the temperature in the range of −5 to 0 degree C., preferably for a period in the range of 0.5 to 1.5 hours and more preferably for 1 hour.

In step (iv) the heating is performed preferably at 80 to 90 degrees C., more preferably 80 to 85 degrees C. The heating is performed preferably during a period of 4 to 6 hours, more preferably for 4 hours.

In step (v) the cooling is performed to a temperature preferably in the range of 35 to 45 degrees C., more preferably 40 degrees C.

In step (vi) the extraction is done using preferably an aliphatic or aromatic nonpolar solvent such as ethylene dichloride, methylene dichloride, hexane and tolunee and more preferably an aromatic nonpolar solvent like tolune.

In step (vii) the aqueous layer is once again heated to a temperature in the range of 80-100 deg C. during a period of 3-8 hrs, aged for 5-8 hrs cooled and re-extracted with toluene.

In an embodiment of the invention the combined organic layers is treated with charcoal for removing any coloring matter present in it In step (x) the distilling of the organic solvent is done preferably between 60-90 deg C. and more preferably between 60-65 deg C. under reduced pressure.

It would be clear from the above description that the process of the present invention could be advantageously employed for the conversion of amides of the general formula 5

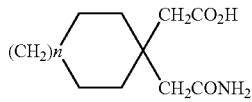

Where n represents a value of 0 to 2 to Lactams of the general formula 6

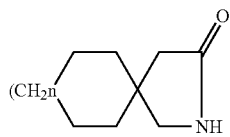

Where in 'n' is an integer with a value of 0-2.

Thus the process of the present invention is found to be very useful for the preparation of gabalactam commercially in the view of the fact that the process straight away yields highly pure (more than 95%)gabalactam in yields greater than 70% of theory.

This process while avoiding the usage of toxic reagents like cyanides, pyrrophoric catalysts, sodium ethoxide and high energy water evaporation processes, yield the gabalactam in a simple, extraction process using low cost material such as bromine and sodium hydroxide. As explained earlier the process of the present invention gives gabalactam of purity over 95%

The details of the invention are given in the Examples given below which are provided to illustrate the invention only and therefore cannot be constructed to limit the scope of the invention.

EXAMPLE-1

Bromine (0.824 kg, 5.15 mole) is added to a solution of sodium hydroxide (1 kg) in water (7 l) at −5to 0degrees C. over 45-90 min and the solution stirred for an additional 30 min at the same temperature. Cyclohexane-1,1-diacetic acid monoamide of the formula 4 (1 kg, 5.02 mole) is added to the above solution in portions over a period of 3 hrs at −5 to 0 degrees and the mixture stirred at the same temperature for 1 hr. The reaction mass is heated to 80-85 degrees C. slowly over a period of 4 hrs and stirred for another 6 hrs at the same temperature. It is then extracted with toluene after cooling the reaction mixture to 40 degree C. twice. The aqueous layer is again heated at 80-85 degrees C., aged for 6 hrs at the same temperature, cooled to 40 degrees C. and extracted with toluene twice. The toluene layers are combined, treated with charcoal and filtered. The filtrate is washed with water twice and evaporated at a temperature of 60-65 degrees C. under vacuum to give white crystals of gabalactam of the formula 1 (0.62 kg, 80.7%), m.p. 88-90 degree C.; purity (area % by HPLC greater than 99).

EXAMPLE-2

Bromine 42 g (0.257 mole) is added to a solution of potassium hydroxide (80 g/80% purity) in water (350 ml) at −5 to 0 degrees C. over 60 min and the solution stirred for an additional 30 min at the same temperature. Cyclohexane-1,1-diacetic acid monoamide of the formula 4 50 g (0.251 mol) is added to the above solution in portions over a period of 2 hrs at −10 to 0 degrees C. and the mixture stirred at the same temperature for 2 hrs. The reaction mass is heated to 90-98 degrees C. slowly over a period of 4 hr and stirred for another 5 hrs at the same temperature. It is then extracted with ethylene dichloride twice, after cooling the reaction mixture to 30 degrees C. The aqueous layer is again heated at 90-98 degrees C. and extracted with ethylene dichloride after cooling the reaction mixture to 30 degrees C., twice. The ethylene dichloride layers are combined, treated with charcoal and filtered. The filtrate is washed with water and evaporated under reduced pressure to give brownish white crystals of gabalactam of the formula 1 (28 g, 72.8%) m.p. 88-90 degree C.; purity (area % by HPLC 98).

EXAMPLE-3

Bromine 45 g (0.257 mole) is added to a solution of sodium hydroxide (45 g) in water (350 ml) at −10 to 0 degrees C. over 45-90 min and the solution stirred for an additional 30 min at the same temperature. Cyclohexane-1,1-diacetic acid monoamide of the formula 4 (50 g, 0.251 mole) is added to the above solution in portions over a period of 1 hr at −5 to 0 degrees C. and the mixture stirred at the same temperature for 1 hr. The reaction mass is heated to 80-90 degrees slowly over a period of 6 hrs and stirred for another 8 hrs at the same temperature. It is then extracted with methylene dichloride twice, after cooling the reaction mixture to 30 degrees C. The aqueous layer is again heated at 80-90 degrees and extracted with methylene dichloride after cooling the reaction mixture to 30 degrees, twice. The methylene dichloride layers are combined, treated with charcoal and filtered. The filtrate is washed with water and evaporated under reduced pressure to give white crystals of gabalactam of the formula 1 (28 g 72.8%) m.p. 88-90 degree C.; purity (area % by HPLC 99).

EXAMPLE 4

Bromine 50 g (0.285 mole) is added to a solution of sodium hydroxide (55 g) in water (300 ml) at −10 to 0 degrees C. over 45-90 min and the solution stirred for an additional 30 min at the same temperature. Cyclohexane-1,1-diacetic acid monoamide of the formula 4 (50 g, 0.251 mole) is added to the above solution in portions over a period of 1.5 hrs at −10 to 0 degrees C. and the mixture stirred at the same temperature for 1 hr. The reaction mass is heated to 85-95 degrees slowly over a period of 5 hrs and stirred for another 7 hrs at the same temperature. It is then extracted with toluene twice, after cooling the reaction mixture to 50 degrees C. The aqueous layer is again heated at 85-95 degrees C. and extracted with toluene after cooling the reaction mixture to 50 degrees C., twice. The toluene layers are combined, treated with charcoal and filtered. The filtrate is washed with water and evaporated under reduced pressure to give white crystals of gabalactam of the formula 1 (29.5 g 76.7%) m.p. 88-90 degree C.; purity (area % by HPLC 98).

We claim:
1. A process for the preparation of gabalactam of formula 1

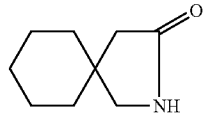

which comprises
(i) preparing an aqueous solution of an alkali or alkaline earth metal hydroxide at a concentration in a range from 10 to 20% by weight, adding bromine to the aqueous solution to yield a corresponding alkali or alkaline earth metal hypobromite solution having a concentration in a range from 5 to 10% by weight,
(ii) adding 1 part by weight of an amide of the formula 4

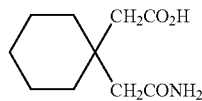

to 7.5 to 9.5 parts by weight of the hypobromite solution during a period in a range from 1 to 4 hours, at a temperature in a range from −10 to +10 degrees C. to form a mixture,
(iii) aging the mixture from step (ii) at a temperature in a range from −10 to +10 degrees C. for a period in a range from 0.5 to 2 hours,
(iv) heating the mixture from step (iii) gradually at a temperature in a range from 80 to 100 degrees C., for a period in a range of 3 to 8 hours and aging for a period in a range from 5 to 8 hours to yield gabalactam,
(v) cooling the mixture of step (iv) at a temperature in a range from 30 to 50 degrees C.,
(vi) extracting the mixture of step (v) using a nonpolar organic solvent or a mixture of nonpolar organic solvents to yield an organic layer containing gabalactam,
(vii) subjecting the resulting aqueous layer to the steps of (iv) to (vi) defined above to yield additional organic layers containing gabalactam,
(viii) combining the organic layers obtained in steps (vi) & (vii) together,
(ix) washing the combined organic layers with water at a temperature in a range from 30 to 35 degrees C., and
(x) distilling of the nonpolar organic solvent or the mixture of nonpolar organic solvents at a temperature in a range from 60 to 110 degrees C., under reduced pressure to yield gabalactam.

2. The process as claimed in claim 1 wherein in step (i) the alkali metal hydroxide is sodium hydroxide.

3. The process as claimed in claim 1 wherein in step (i) the concentration of the alkali or alkaline earth metal hydroxide solution is in the range from 10 to 15%.

4. The process as claimed in claim 1 wherein in step (i) the concentration of the hypobromite solution is in the range from 5 to 8%.

5. The process as claimed in claim 1 wherein in step (ii) the amount of the hypobromite solution used is in the range from 8 to 9 parts of the hypobromite solution.

6. The process as claimed in claim 1 wherein in step (ii) the adding is performed during the period in the range from 1 to 3 hours.

7. The process as claimed in claim 1 wherein in step (ii) the temperature employed during the adding is maintained at the range from −5 to +5 degrees C.

8. The process as claimed in claim 1 wherein in step (iii) the aging of the mixture is performed at the temperature in the range from −5 to 0 degrees C. for the period in the range from 0.5 to 1.5 hours.

9. The process as claimed in claim 1 wherein in step (iv) the heating is performed at the temperature in the range from 80 to 90 degrees C.

10. The process as claimed in claim 9 wherein in step (iv) the heating is performed for the period in the range from 4 to 6 hours.

11. The process as claimed in claim 1 wherein in step (v) the cooling is performed at the temperature in the range from 35 to 45 degrees C.

12. The process as claimed in claim 1 wherein in step (vi) the nonpolar organic solvent and the mixture of nonpolar organic solvents are selected from the group consisting of ethylene dichloride, methylene dichloride, hexane and toluene.

13. The process as claimed in claim 1 wherein in step (vii) the aqueous layer is once again heated at a temperature in a range from 80 to 100 degrees C. during a period of 3 to 8 hours, aged for 5 to 8 hours, cooled and re-extracted with toluene.

14. The process as claimed in claim 1 wherein in step (viii) the combined organic layers are treated with charcoal for removing any coloring matter present.

15. The process as claimed in claim 1 wherein in step (x) the distilling of the nonpolar organic solvent or the mixture of nonpolar organic solvents is performed at the temperature in the range from 60 to 90 degrees C. under reduced pressure.

16. A process for the preparation of gabalactam of formula 1

which comprises
(i) preparing an aqueous solution of sodium hydroxide at a concentration in a range from 10 to 15% by weight, adding bromine to the aqueous solution to yield a corresponding sodium hypobromite solution having a concentration in a range from 5 to 8% by weight,
(ii) adding 1 part by weight of an amide of the formula 4

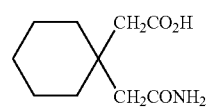

to 8 to 9 parts by weight of the hypobromite solution during a period in a range from 1 to 2 hours, at a temperature in a range from −5 to +5 degrees C. to form a mixture,
(iii) aging the mixture from step (ii) at a temperature in a range from −5 to 0 degrees C. for a period in a range from 0.5 to 1.5 hours,
(iv) heating the mixture from step (iii) gradually at a temperature in a range from 80 to 90 degrees C., for a period in a range of 4 to 6 hours and aging for a period in a range from 5 to 8 hours to yield gabalactam, (v) cooling the mixture of step (iv) at a temperature in a range from 35 to 45 degrees C., (vi) extracting the mixture of step (v) using toluene to yield an organic layer containing gabalactam, (vii) subjecting the resulting aqueous layer to the steps of (iv) to (vi) defined above to yield additional organic layers containing gabalactam, (viii) combining the organic layers obtained in steps (vi) & (vii) together, (ix) washing the combined organic layers with water at a temperature in a range from 30 to 35 degrees C., and (x) distilling of toluene at a temperature in a range from 60 to 65 degrees C., under reduced pressure to yield gabalactam.

* * * * *